United States Patent [19]

Anderson et al.

[11] 4,332,944

[45] Jun. 1, 1982

[54] COMPOSITIONS AND USE

[75] Inventors: Richard J. Anderson, Palo Alto; Michael M. Leippe, Boulder Creek, both of Calif.

[73] Assignee: Zoecon Corporation, Palo Alto, Calif.

[21] Appl. No.: 281,808

[22] Filed: Jul. 9, 1981

[51] Int. Cl.³ .................... A01N 43/40; C07D 401/12
[52] U.S. Cl. ......................................... 546/272; 71/94
[58] Field of Search ............................ 546/272; 71/94

[56] References Cited

U.S. PATENT DOCUMENTS 4,225,497  9/1980  Baudowin et al. ............. 546/272 X

*Primary Examiner*—Richard Raymond
*Attorney, Agent, or Firm*—Jacqueline S. Larson; Donald W. Erickson; Thomas T. Gordon

[57] ABSTRACT

N-substituted phenyl tetrahydrophthalimides, intermediates therefor and synthesis thereof, which compounds are useful herbicides.

20 Claims, No Drawings

COMPOSITIONS AND USE

This invention relates to N-substituted phenyl tetrahydrophthalimides, intermediates therefor and synthesis thereof, which compounds are useful herbicides.

The N-substituted phenyl tetrahydrophthalimides of the present invention are represented by the following formula (A):

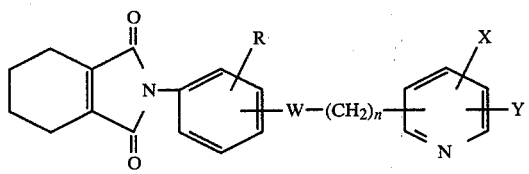

wherein, n is one, two or three;

R is hydrogen, bromo, chloro, fluoro or iodo;

W is oxygen or sulfur; and each of X and Y is, independently, selected from hydrogen, bromo, chloro, fluoro, iodo, lower alkyl, lower alkoxy, lower thioalkyl, lower haloalkoxy, nitro, lower alkoxycarbonyl and cyano.

Hereinafter, each of n, R, W, X and Y is as defined above, unless otherwise specified.

The compounds of formula A are prepared by the reaction of 3,4,5,6-tetrahydrophthalic anhydride with a substituted aniline of formula (I).

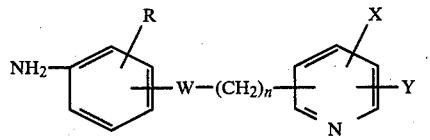

The reaction is conducted at a temperature above room temperature such as the reflux temperature of the reaction mixture and is generally complete within a few hours or less.

The substituted aniline compounds of formula (I) wherein W is oxygen can be prepared by the reaction of nitrophenol with a substituted pyridylalkyl halide to obtain the corresponding substituted nitrobenzene which is reduced to the desired substituted aniline of formula (I). For example, the reaction of 4-nitrophenol and 6-chloro-3-pyridylmethyl bromide gives 4-(2-chloro-5-pyridylmethyloxy)nitrobenzene which is then reduced to 4-(2-chloro-5-pyridylmethyloxy)aniline of formula I. Alternatively, the compounds of formula I can be prepared by the reaction of a halo-nitrobenzene with a substituted pyridylalkyl alcohol or substituted pyridylalkyl thiol followed by reduction of the nitro group. For example, the reaction of 4-fluoronitrobenzene and 5-bromo-2-pyridine methanol gives 4-(5-bromo-2-pyridylmethyloxy)nitrobenzene which is then reduced using, for example, iron powder to give 4-(5-bromo-2-pyridylmethyloxy)aniline.

The compounds of formula A may also be prepared by the reaction of a pyridylalkyl halide with a 3,4,5,6-tetrahydrophthalimidophenol of formula (II).

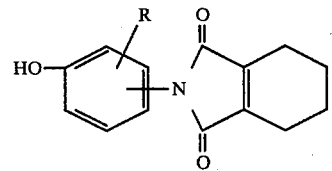

The alcohol of formula II may be prepared by reacting together aminophenol and 3,4,5,6-tetrahydrophthalic anhydride.

The following terms, wherever used in the description herein and in the appended claims, have the meaning defined below, unless otherwise specified hereinafter.

The term "lower alkyl," as used herein, refer to an alkyl group of one to six carbon atoms.

The term "lower alkoxy," as used herein, refers to an alkoxy group of one to six carbon atoms.

The term "lower alkoxycarbonyl," as used herein, refers to an alkoxycarbonyl group of two to six carbon atoms.

The term "lower thioalkyl," as used herein, refers to a thioalkyl group of one to six carbon atoms such as methylthio.

The term "lower haloalkyl," as used herein, refers to a haloalkyl group of one to six carbon atoms substituted with at least one halo atom such as trifluoromethyl, difluoromethyl, trichloromethyl, dichloromethyl, fluoromethyl or chloromethyl.

The term "lower haloalkoxy," as used herein, refers to a haloalkoxy group of one to six carbon atoms substituted with at least one halo atom such as difluoromethoxy, dichloromethoxy, trifluoromethoxy, trichloromethoxy, fluoromethoxy or chloromethoxy.

The compounds of formula (A) are useful for the control of weeds using pre- and/or post-emergent treatments. The compounds can be applied in the form of dusts, granules, solutions, emulsions, wettable powders and suspensions. Application of a compound of the present invention is made according to conventional procedure using from about one-forth to ten pounds per acre. Methods of preparing herbicidal formulations which can be used with a compound of the present invention are described in the literature along with suitable liquid and solid carriers such as in U.S. Pat. Nos. 4,192,669, 4,163,661 and 4,072,499 which are incorporated herein by reference. The compounds of the present invention have activity on broadleaf plants and grassy plants. The optimum usage of a compound of the present invention is readily determinable by one of ordinary skill in the art using routine testing such as greenhouse testing and small plot testing.

In another embodiment of the present invention, there are provided compounds of formula (B) and (C) which have useful herbicidal activity.

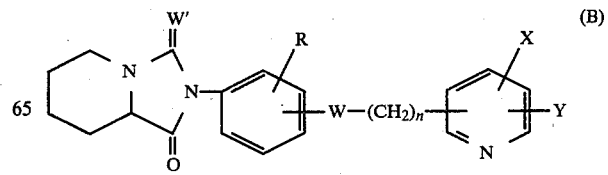

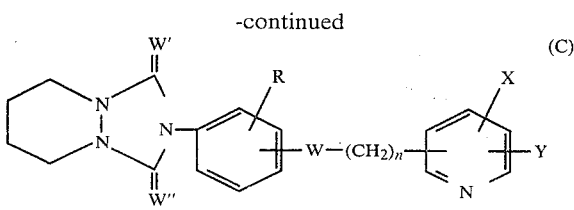

In the above formulas, each of W' and W'' is oxygen or sulfur and each of R, n, W, X and Y is as defined hereinabove.

The following examples are provided to illustrate the practice of the present invention. Temperature is given in degrees centigrade. All parts are by weight unless otherwise indicated. RT means room temperature.

EXAMPLE 1

6-Chloronicotinic acid (3.0 g, 18.98 mmol) is dissolved in 30 ml of tetrahydrofuran (THF), with the temperature of the solution maintained below 30°. A 1 M solution of borane/TMF (19 ml, 19.0 mmol) is added at a rate to maintain a slow evolution of gas. This mixture is stirred at RT overnight. The reaction is poured onto approximately 50 g ice with 2 ml concentrated hydrochloric acid and is stirred for 1 hour. The pH of the reaction is adjusted to 5. The reaction is then extracted with chloroform, washed with water, dried and stripped to give 6-chloro-3-pyridinemethanol. A mixture of this pyridinemethanol (2.5 g, 17.4 mmol) and 1-fluoro- 4-nitrobenzene (2.4 g, 17.4 mmol), dissolved together in 15 ml of THF, is added to a stirring suspension of sodium hydride (0.42 g, 17.4 mmol) in 25 ml of THF at a rate to maintain the temperature below 32°. The mixture is stirred for 1 hour, then diluted with water, extracted with chloroform, washed with water, dried and stripped to give 2-chloro-5-(4-nitrophenoxy)-methylpyridine.

Alternatively, 2-chloro-5-(4-nitrophenoxy)methylpyridine may be prepared by heating to 80° for 24 hours a mixture of 2-chloro-(5-chloromethyl)pyridine hydrochloride (2.0 g, 10.2 mmol), 4-nitrophenol (1.5 g, 10.2 mmol), potassium carbonate (2.8 g, 20.4 mmol) and potassium iodide (50 mg) in 40 ml of a 1:1 mixture of isopropanol and dimethylformamide. The resulting reaction mixture is poured into water, extracted with ether, washed with water, dried and stripped to give 2-chloro-5-(4-nitrophenoxy)methylpyridine.

Two grams (7.6 mmol) of 2-chloro-5-(4-nitrophenoxy) methylpyridine and 4 grams (76.0 mmol) of ammonium chloride in 40 ml of ethanol and 20 ml of water are heated to 60°, after which 2.1 grams (38.0 mmol) of iron powder is added in small portions over 15 minutes. The mixture is heated under reflux for 2 hours. The reaction is cooled and stripped, and the residue is taken up in ether, washed with water, dried over sodium sulfate and stripped to yield 2-chloro-5-(4-aminophenoxy)methylpyridine.

A mixture of 2-chloro-5-(4-aminophenoxy)methylpyridine (1.0 g, 4.26 mmol) and 3,4,5,6-tetrahydrophthalic anhydride (0.65 g, 4.26 mmol) is heated under reflux in 20 ml acetic acid for 1 hour. The reaction is cooled and stripped, and the residue is taken up in chloroform, washed with water, dried and stripped to give the final product N-4-[5-(2-chloropyridyl)methoxy]phenyl-3,4,5,6-tetrahydrophthalimide.

EXAMPLE 2

Following the procedure of Example 1, 2-chloro-5-(4-nitrophenoxy)ethylpyridine is prepared from the reaction of 2-chloro-5-pyridylacetic acid with borane/THF and 1-fluoro-4-nitrobenzene or, alternatively, from the reaction of 2-chloro-(5-chloroethyl)pyridine with 4 nitrophenol. The resulting 2-chloro-5-(4-nitrophenoxy)ethylpyridine is reduced with iron in the presence of NH4Cl to produce 2-chloro-5-(4-aminophenoxy)-ethylpyridine, which in turn is reacted with 3,4,5,6-tetra-hydrophthalic anhydride to yield the final product N-4-[5-(2-chloropyridyl)ethoxy]phenyl-3,4,5,6-tetrahydrophthalimide.

EXAMPLE 3

Following the procedure of Example 1, each of the substituted methylpyridines in column I is prepared from the corresponding substituted nicotinic acid and is then reacted with 3,4,5,6-tetrahydrophthalic anhydride to yield the compound of formula (A) in column II.

I 3-(4-aminophenoxy)methylpyridine
2-trifluoromethyl-5-(4-aminophenoxy)-methylpyridine
3-chloro-5-(4-aminophenoxy)methylpyridine
2-bromo-5-(4-aminophenoxy)methylpyridine
2-chloro-3-methyl-5-(4-aminophenoxy)methylpyridine.

II

N-4-(3-pyridylmethoxy)phenyl-3,4,5,6-tetrahydrophthalimide

N-4-[5-(2-trifluoromethylpyridyl)methoxy]phenyl-3,4,5,6-tetrahydrophthalimide

N-4-[5-(3-chloropyridyl)methoxy]phenyl-3,4,5,6-tetrahydrophthalimide

N-4-[5-(2-bromopyridyl)methoxy]phenyl-3,4,5,6-tetrahydrophthalimide

N-4-[5-(2-chloro-3-methylpyridyl)methoxy]phenyl-3,4,5,6-tetrahydrophthalimide

EXAMPLE 4

Following the procedure of Example 1, 5-chloro-2-pyridinemethanol, prepared from 5-chloropicolinic acid, is reacted with 1-fluoro-4-nitrobenzene to give 5-chloro-2-(4-nitrophenoxy)methylpyridine, which is converted to 5-chloro-2-(4-aminophenoxy)methylpyridine by reduction with iron and ammonium chloride. The 5-chloro-2-(4-aminophenoxy)methylpyridine and 3,4,5,6-tetrahydrophthalic anhydride are reacted to yield the final product N-4-[2-(5-chloropyridyl)methoxy]phenyl-3,4,5,6-tetrahydrophthalimide.

In like manner, each of 2-(4-aminophenoxy)methylpyridine and 5-trifluoromethyl-2-(4-aminophenoxy)methylpyridine, prepared from, respectively, picolinic acid and 5-trifluoromethylpicolinic acid, is reacted with 3,4,5,6-tetrahydrophthalic anhydride to yield N-4-(2-pyridylmethoxy)phenyl-3,4,5,6-tetrahydrophthalimide and N-4-[2-(5-trifluoromethylpyridyl)methoxy]phenyl-3,4,5,6-tetrahydrophthalimide, respectively.

As an alternative method, each of 5-chloro-2-(4-aminophenoxy)methylpyridine, 2-(4-aminophenoxy)-methylpyridine and 5-trifluoromethyl-2-(4-aminophenoxy)methylpyridine may be prepared from the reaction of 4-nitrophenol with, respectively, 5-chloro-(2-chloromethyl)pyridine, (2-chloromethyl)pyridine and 5-trifluoromethyl-(2-chloromethyl)-pyridine followed by reduction with iron and ammonium chloride, following the procedure of Example 1.

EXAMPLE 5

2-Chloro-4-nitrophenol (17.4 mmol) in 15 ml of THF is slowly added to a stirring suspension of sodium hydride (17.4 mmol) in 25 ml of THF. After gas evolution has ceased, 2-chloro-5-bromomethylpyridine is added and the mixture is heated under reflux overnight. The reaction is diluted with water, extracted with chloroform, washed with water, dried and stripped to give 2-chloro-5-(2-chloro-4-nitrophenoxy)methylpyridine.

Following the procedure of Example 1, 2-chloro-5-(2-chloro-4-nitrophenoxy)methylpyridine is reduced to 2-chloro-5-(2-chloro-4-aminophenoxy)methylpyridine, which is then reacted with 3,4,5,6-tetrahydrophthalic anhydride to yield N- 3-chloro-4-[5-(2-chloropyridyl)-methoxy]phenyl-3,4,5,6-tetrahydrophthalimide.

In like manner, each of 3-bromomethylpyridine and 5-chloro-2-bromomethylpyridine is reacted with 2-chloro-4-nitrophenol to give 3-(2-chloro-4-nitrophenoxy)methylpyridine and 5-chloro-2-(2-4-nitrophenoxy)-methylpyridine, respectively, each of which is reduced. The resulting 3-(2-chloro-4-aminophenoxy)methylpyridine and 5-chloro-2-(2-chloro-4-aminophenoxy)methylpyridine is each reacted with 3,4,5,6-tetrahydrophthalic anhydride to yield, respectively, N-3-chloro-4-(3-pyridylmethoxy)phenyl-3,4,5,6-tetrahydrophthalimide and N-3-chloro-4-[2-(5-chloropyridyl)methoxy]phenyl-3,4,5,6-tetrahydrophthalmide.

EXAMPLE 6

To a mixture of 3-nitrophenol (5 mmol) and potassium carbonate (10 mmol) in dimethylformamide is added 2-chloro-(3-bromomethyl)pyridine (5 mmol). This mixture is heated to 80° for 24 hours and is then poured into water, extracted with ether, washed, dried and stripped to give 2-chloro-5-(3-nitrophenoxy)methylpyridine, which is reduced following the procedures of Example 1 to 2-chloro-5-(3-aminophenoxy)methylpyridine. The 2-chloro-5-(3-aminophenoxy)methylpyridine is then reacted with 3,4,5,6-tetrahydrophthalic anhydride to yield N-3-[5-(2-chloropyridyl)methoxy]phenyl-3,4,5,6-tetrahydrophthalimide.

EXAMPLE 7

Following the procedure of Example 5, each of 2-chloro-5-(4-aminophenylthio)methylpyridine and 5-chloro-2-(4-aminophenylthio)methylpyridine is prepared from the reaction of 4-nitrobenzenethiol with, respectively, 2-chloro-5-bromomethylpyridine and 5-chloro-2-bromomethylpyridine, followed by reduction. Each of 2-chloro-5-(4-aminophenylthio)methylpyridine and 5-chloro-2-(4-aminophenylthio)methylpyridine is reacted with 3,4,5,6-tetrahydrophthalic anhydride to yield N-4-[5-(2-chloropyridyl)methylthio]phenyl-3,4,5,6-tetrahydrophthalimide and N-4-[2-(5-chloropyridyl)methylthio]phenyl-3,4,5,6-tetrahydrophthalimide, respectively.

What is claimed is:

1. A compound selected from those of the following formula (A):

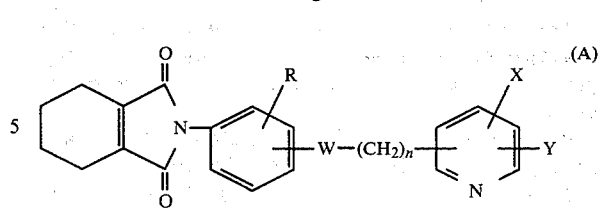

wherein,
n is one, two or three;
R is hydrogen, bromo, chloro, fluoro or iodo;
W is oxygen or sulfur; and
each of X and Y is, independently, selected from hydrogen, bromo, chloro, fluoro, iodo, lower alkyl, lower alkoxy, lower thioalkyl, lower haloalkyl, lower haloalkoxy, nitro, lower alkoxycarbonyl and cyano.

2. A compound according to claim 1 of the formula:

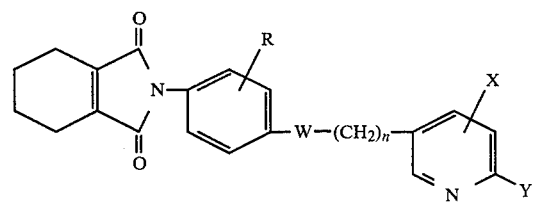

3. A compound according to claim 1 of the formula:

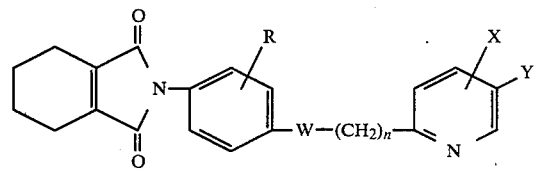

4. A compound according to claim 1 of the formula:

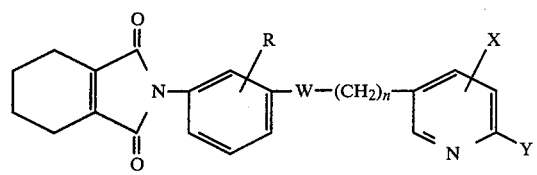

5. A compound according to claim 1 of the formula:

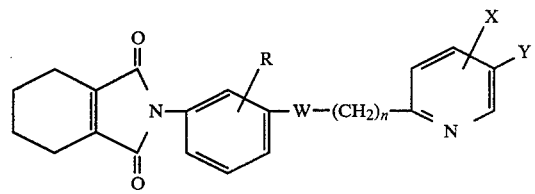

6. A compound according to claim 1 wherein R is hydrogen or chloro, n is one and each of X and Y is independently selected from hydrogen and chloro.

7. A compound according to claim 6 wherein R is hydrogen, W is oxygen, X is hydrogen and Y is chloro.

8. A compound according to claim 2 wherein R is hydrogen or chloro, W is oxygen, n is one, X is hydrogen, chloro or methyl and Y is hydrogen, bromo or chloro.

9. A compound according to claim 8 wherein R is hydrogen, X is hydrogen and Y is chloro.

10. A compound according to claim 8 wherein each of R, X and Y is hydrogen.

11. A compound according to claim 8 wherein R is chloro and is in the 3 position, X is hydrogen and Y is bromo or chloro.

12. A compound according to claim 3 wherein R is hydrogen or chloro, W is oxygen, n is one, X is hydrogen, chloro or methyl and Y is hydrogen, bromo or chloro.

13. A compound according to claim 12 wherein R is hydrogen, X is hydrogen and Y is chloro.

14. A compound according to claim 12 wherein each of R, X and Y is hydrogen.

15. A compound according to claim 12 wherein R is chloro and is in the 3 position, X is hydrogen and Y is bromo or chloro.

16. A compound according to claim 4 wherein R is hydrogen or chloro, W is oxygen, n is one, X is hydrogen, chloro or methyl, and Y is hydrogen, bromo or chloro.

17. A compound according to claim 16 wherein R is hydrogen, X is hydrogen and Y is bromo or chloro.

18. A compound according to claim 5 wherein R is hydrogen or chloro, W is oxygen, n is one, X is hydrogen, chloro or methyl, and Y is hydrogen, bromo or chloro.

19. A compound according to claim 18 wherein R is hydrogen, X is hydrogen and Y is bromo or chloro.

20. A method for the control of weeds which comprises treating said weed with a herbicidally effective amount of a compound according to formula (A) herein.

* * * * *